(12) United States Patent
Bendall et al.

(10) Patent No.: US 8,422,030 B2
(45) Date of Patent: Apr. 16, 2013

(54) FRINGE PROJECTION SYSTEM WITH INTENSITY MODULATING BY COLUMNS OF A PLURALITY OF GRATING ELEMENTS

(75) Inventors: Clark Alexander Bendall, Syracuse, NY (US); Theodore Alexander Chilek, Skaneateles, NY (US)

(73) Assignee: General Electric Company, Schenectady, NY (US)

( * ) Notice: Subject to any disclaimer, the term of this patent is extended or adjusted under 35 U.S.C. 154(b) by 58 days.

(21) Appl. No.: 13/100,826

(22) Filed: May 4, 2011

(65) Prior Publication Data
US 2011/0205552 A1 Aug. 25, 2011

Related U.S. Application Data

(63) Continuation-in-part of application No. 12/249,513, filed on Oct. 10, 2008, now Pat. No. 8,107,083, and a continuation-in-part of application No. 12/042,821, filed on Mar. 5, 2008, now Pat. No. 7,821,649.

(51) Int. Cl.
*G01B 11/24* (2006.01)
*G01N 21/55* (2006.01)

(52) U.S. Cl.
USPC .......................................... 356/606; 356/447

(58) Field of Classification Search .................. 356/445, 356/447, 457, 458, 489, 496, 511, 512, 600–626
See application file for complete search history.

(56) References Cited

U.S. PATENT DOCUMENTS

| | | | |
|---|---|---|---|
| 4,988,886 A | 1/1991 | Palum et al. |
| 5,066,119 A | 11/1991 | Bertrand |
| 5,069,548 A | 12/1991 | Boehnlein |
| 5,135,308 A | 8/1992 | Kuchel |
| 5,135,309 A | 8/1992 | Kuchel et al. |
| 5,175,601 A | 12/1992 | Fitts |
| 5,289,264 A | 2/1994 | Steinbichler |
| 5,302,999 A | 4/1994 | Oshida et al. |
| 5,307,152 A | 4/1994 | Boehnlein et al. |
| 5,386,292 A | 1/1995 | Massen et al. |
| 5,434,669 A | 7/1995 | Tabata et al. |
| 5,581,352 A | 12/1996 | Zeien |
| 5,636,025 A | 6/1997 | Bieman et al. |
| 5,810,719 A | 9/1998 | Toida |
| 5,823,942 A | 10/1998 | Toida |
| 5,835,218 A | 11/1998 | Harding |
| 5,847,832 A | 12/1998 | Liskow et al. |
| 6,011,624 A | 1/2000 | de Groot |
| 6,084,712 A | 7/2000 | Harding |

(Continued)

FOREIGN PATENT DOCUMENTS

EP 2272417 A1 1/2011
JP 59192223 A 10/1984

OTHER PUBLICATIONS

EP Search Report issued in connection with corresponding EP Patent Application No. 09165205.7 filed on Jul. 10, 2009.

(Continued)

*Primary Examiner* — Hwa Lee
(74) *Attorney, Agent, or Firm* — Hiscock & Barclay LLP

(57) ABSTRACT

An intensity modulating element for a probe having a plurality of light emitters for phase-shift analysis and measurement is disclosed. The intensity modulating element comprises a plurality of columns of a plurality of grating elements formed by two opposing patterns.

20 Claims, 13 Drawing Sheets

U.S. PATENT DOCUMENTS

| | | |
|---|---|---|
| 6,088,105 A | 7/2000 | Link |
| 6,100,984 A | 8/2000 | Chen et al. |
| 6,252,623 B1 | 6/2001 | Lu et al. |
| 6,291,817 B1 | 9/2001 | Kobayashi et al. |
| 6,438,272 B1 | 8/2002 | Huang et al. |
| 6,950,191 B2 | 9/2005 | Ge |
| 6,977,732 B2 | 12/2005 | Chen et al. |
| 7,170,677 B1 | 1/2007 | Bendall et al. |
| 7,286,246 B2 | 10/2007 | Yoshida |
| 7,302,109 B2 | 11/2007 | Hu et al. |
| 7,369,253 B2 | 5/2008 | Zwemer et al. |
| 7,388,679 B2 | 6/2008 | Yoshino et al. |
| 7,433,058 B2 | 10/2008 | Cantin et al. |
| 7,551,293 B2 | 6/2009 | Yelin et al. |
| 7,570,370 B2 | 8/2009 | Steinbichler et al. |
| 7,812,968 B2 | 10/2010 | Bendall et al. |
| 7,821,649 B2 | 10/2010 | Bendall et al. |
| 8,313,197 B2 * | 11/2012 | Lee et al. ............ 353/28 |
| 2002/0163573 A1 | 11/2002 | Bieman et al. |
| 2003/0043387 A1 | 3/2003 | Lim et al. |
| 2004/0105100 A1 | 6/2004 | Shirley |
| 2005/0046872 A1 | 3/2005 | Hu et al. |
| 2005/0088529 A1 | 4/2005 | Geng |
| 2005/0099638 A1 | 5/2005 | Quadling et al. |
| 2006/0072122 A1 | 4/2006 | Hu et al. |
| 2006/0132790 A1 | 6/2006 | Gutin |
| 2006/0282009 A1 | 12/2006 | Oberg et al. |
| 2007/0090308 A1 | 4/2007 | Harding |
| 2007/0091320 A1 | 4/2007 | Hu et al. |
| 2007/0109558 A1 | 5/2007 | Harding et al. |
| 2008/0208006 A1 | 8/2008 | Farr |
| 2009/0225320 A1 | 9/2009 | Bendall et al. |
| 2009/0225321 A1 | 9/2009 | Bendall et al. |
| 2009/0225329 A1 | 9/2009 | Bendall et al. |
| 2009/0225333 A1 | 9/2009 | Bendall et al. |

OTHER PUBLICATIONS

Bieman et al., "Absolute Measurement Using Field Shift Moire," SPIE Proceedings vol. 1614, Optics, Illumination and Image Sensing for Machine Vision VI, Boston, Massachusetts, Nov. 1991.

Boehnlein et al., "Field Shift Moire, a New Technique for Absolute Range Measurement," SPIE Conference 1163, Fringe Analysis Methods, San Diego, California, Aug. 1989.

Harding, "Latest Optical Methods for Industrial Dimensional Metrology" Proceedings SPIE vol. 6000, 600001, Two-and Three-Dimensional Methods for Inspection and Metrology III, 2005.

Harding et al., "Machine Vision Method for Small Feature Measurements," Tang Publication: Proc. SPIE vol. 5606, Two- and Three-Dimensional Vision Systems for Inspection, Control, and Metrology II; 2004.

Search Report and Written Opinion from EP Application No. 12166473.4 dated Jul. 27, 2012.

* cited by examiner

☒ Emitter group 1
☰ Emitter group 2
☐ Emitter group 3

Emitter 1
Emitter 2
Emitter 3

FRINGE PROJECTION SYSTEM WITH INTENSITY MODULATING BY COLUMNS OF A PLURALITY OF GRATING ELEMENTS

CROSS-REFERENCE TO RELATED APPLICATIONS

This application is a continuation-in-part of and claims priority from U.S. application Ser. No. 12/249,513, filed Oct. 10, 2008, entitled System Aspects for a Probe System that Utilizes Structured Light, which is a continuation-in-part of and claims priority from U.S. application Ser. No. 12/042,821, now U.S. Pat. No. 7,821,649, filed Mar. 5, 2008 and issued Oct. 26, 2010, entitled Fringe Projection System and Method for a Probe Suitable for Phase-Shift Analysis, the entirety of each of the above applications which are incorporated herein by reference.

BACKGROUND OF THE INVENTION

The subject matter described herein relates generally to borescopes and endoscopes, and more particularly, to a borescope/endoscope which provides 3D surface mapping and dimensional measurement using an intensity modulating element.

Borescopes and endoscopes are typically used for inspection inside a remote cavity. Most borescopes/endoscopes, referred to herein as probes, employ an external light source coupled to fiber optic bundles in the probe to provide illumination of a remote object or surface at the distal end. When the object is illuminated, an internal image is formed by a lens system on an image sensor, and the image is relayed to a connected display, such as a video screen. The image sensor may be located at the proximal end of the probe, as with an optical rigid borescope or fiberscope, or at the distal end as with a video borescope or endoscope. Such systems are often used to inspect in inaccessible locations for damage or wear or to verify that parts have been properly manufactured or assembled. Among other things, it is desirable to obtain dimensional measurements to verify that damage or wear does not exceed an operational limit or that a manufactured part or assembly meets its specifications. It may also be desirable to produce a 3D model or surface map for comparison to a reference, 3D viewing, reverse engineering, or detailed surface analysis.

The image shown on the connected display varies in magnification and apparent size depending upon the distance between the object and the distal end of the probe. This leads to difficulties in directly determining dimensional measurements, especially in three spatial dimensions.

There are a number of known approaches for providing 3D data through a probe including splitting the view to gain a stereo image (stereo viewing), projecting a coarse pattern of dots onto the remote object, or using a single line to obtain a single image profile. Stereo methods can be used to create a 3D view, but can only provide information where two points on the image can be correlated. This can be problematic when little surface detail exists. The correlation process can also require significant processing, so producing a full 3D surface map can be time consuming. It is more typical to only correlate a small number of points needed for basic measurements. Projecting a course pattern of dots permits measurement to be obtained at the points of the dots. However, the areas between the dots are left to be interpolated, so any surface variations between them are lost. Finally, a single line profile provides useful information along that single profile, but proper positioning of the single line on the object of interest can be difficult, and measurements that require non co-linear points, such as point to line or area measurements, are subject to error if the surface is not flat or the view is not perpendicular to the surface. The scanning of a single profile line that is often employed in commercial systems to build a 3D surface map is generally not practical in a small probe due to size constraints.

Other limitations also exist regarding the approaches discussed above. For example, a large computing capacity is often required to implement the solutions, and highly skilled technicians are needed to operate the equipment. In addition, the above approaches may not be appropriate when a dense 3D full surface map or full-field object measurement is desired. Without the full-field data, imperfections on a surface or object may be missed entirely. Thus, it is desirable to provide a probe that offers full-field surface mapping.

Full-field object data can be obtained through phase-shifting. Phase-shifting is an analysis technique used for non-contact optical metrology applications. Phase-shifting typically involves projecting one or more sets of parallel lines that cross the field of view (FOV) of a camera. As the object distance changes, the parallel lines, or fringe sets, shift across the FOV. Which line is which, or absolute phase, must be determined in order to make accurate measurements and obtain an accurate surface map. The absolute phase at a given point in the image is defined as the total phase difference ($2\pi$ times the number of line periods) between a reference point in the projected line pattern and the given point. The reference point can be arbitrarily defined.

There are a number of known approaches to decipher which line is which and determine absolute phase. Some approaches include employing multiple fringe sets with physical horizontal offsets resulting in a relative phase that changes with distance or using multiple fringe sets with physical axial offsets to change the period with distance. Most techniques use additional projections. For example, to assist in determining the absolute phase an extra line may be projected to give a starting reference point. The determined absolute phase combined with the fringe set position in the FOV are commonly used to determine absolute object distance.

Phase-shifting methods have not been practical for use in devices such as borescopes and endoscopes. The equipment required to project suitable line patterns for phase-shifting methods usually include a projector, scanner, piezo mirror, or similar item. Among other things, the size limitations of probes make the use of typical equipment mechanically challenging.

Thus, it is desirable to provide a practical mechanical configuration of a probe that is able to perform measurements and 3D surface mapping based on phase-shift analysis.

The discussion above is merely provided for general background information and is not intended to be used as an aid in determining the scope of the claimed subject matter.

BRIEF DESCRIPTION OF THE INVENTION

An intensity modulating element for a probe having a plurality of light emitters for phase-shift analysis and measurement is disclosed. The intensity modulating element comprises a plurality of columns of a plurality of grating elements formed by two opposing patterns. An advantage that may be realized in the practice of some disclosed embodiments of the intensity modulating element is more accurate phase-shift analysis.

In one exemplary embodiment, a probe is disclosed. The probe comprises an insertion tube, a plurality of light emitters disposed in parallel on the distal end of the insertion tube, wherein the plurality of light emitters are spaced apart along an axis perpendicular to the light emitters, at least one intensity modulating element comprising a plurality of columns of a plurality of grating elements having a grating period, wherein the plurality of columns of the plurality of grating elements are parallel to the plurality of light emitters, and wherein the light from the plurality of light emitters is passed through the at least one intensity modulating element to project a plurality of fringe sets onto a surface, each of the plurality of fringe sets comprising a structured-light pattern projected when one emitter group of at least one of the plurality of light emitters is emitting, an imager for obtaining at least one image of the surface; a processing unit that is configured to perform phase-shift analysis on the at least one image, an inspection light delivery system which delivers light from an inspection light source to the surface; wherein the inspection light delivery system outputs light from the distal end of the insertion tube during inspection mode, wherein the intensity of light output from the inspection light delivery system is automatically decreased during measurement mode, and wherein the probe operates in measurement mode when at least one of the plurality of fringe sets is projected onto the surface.

In another exemplary embodiment, an intensity modulating element is disclosed. The intensity modulating element comprises a plurality of columns of a plurality of grating elements having a grating period, wherein the plurality of columns of the plurality of grating elements are parallel to the plurality of light emitters, a first continuous sinusoidal pattern extending perpendicular to the plurality of light emitters forming the top side of each of the plurality of grating elements, a second continuous sinusoidal pattern extending perpendicular to the plurality of light emitters forming the bottom side of each of the plurality of grating elements, wherein the second continuous sinusoidal pattern opposes and is the mirror image of the first continuous sinusoidal pattern, and wherein the plurality of grating elements form a plurality of rows of grating elements extending for several grating periods of the first continuous sinusoidal pattern perpendicular to the plurality of light emitters.

In another exemplary embodiment, the intensity modulating element comprises a plurality of columns of a plurality of grating elements having a grating period, wherein the plurality of columns of the plurality of grating elements are parallel to the plurality of light emitters, a first intermittent sinusoidal pattern extending perpendicular to the plurality of light emitters forming the top side of each of the plurality of grating elements, a second intermittent sinusoidal pattern extending perpendicular to the plurality of light emitters forming the bottom side of each of the plurality of grating elements, wherein the second intermittent sinusoidal pattern opposes and is the minor image of the first intermittent sinusoidal pattern, a left side and a right side truncating the first intermittent sinusoidal pattern and the second sinusoidal pattern for each of the plurality of grating elements, wherein the plurality of grating elements in the plurality of columns are connected by a web extending from the top side of one grating element to the bottom side of an adjacent grating element, and wherein the plurality of grating elements form a plurality of rows of grating elements extending for several grating periods of the first intermittent sinusoidal pattern perpendicular to the plurality of light emitters forming a gap between the left side of one grating element and the right side of an adjacent grating element in the row.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
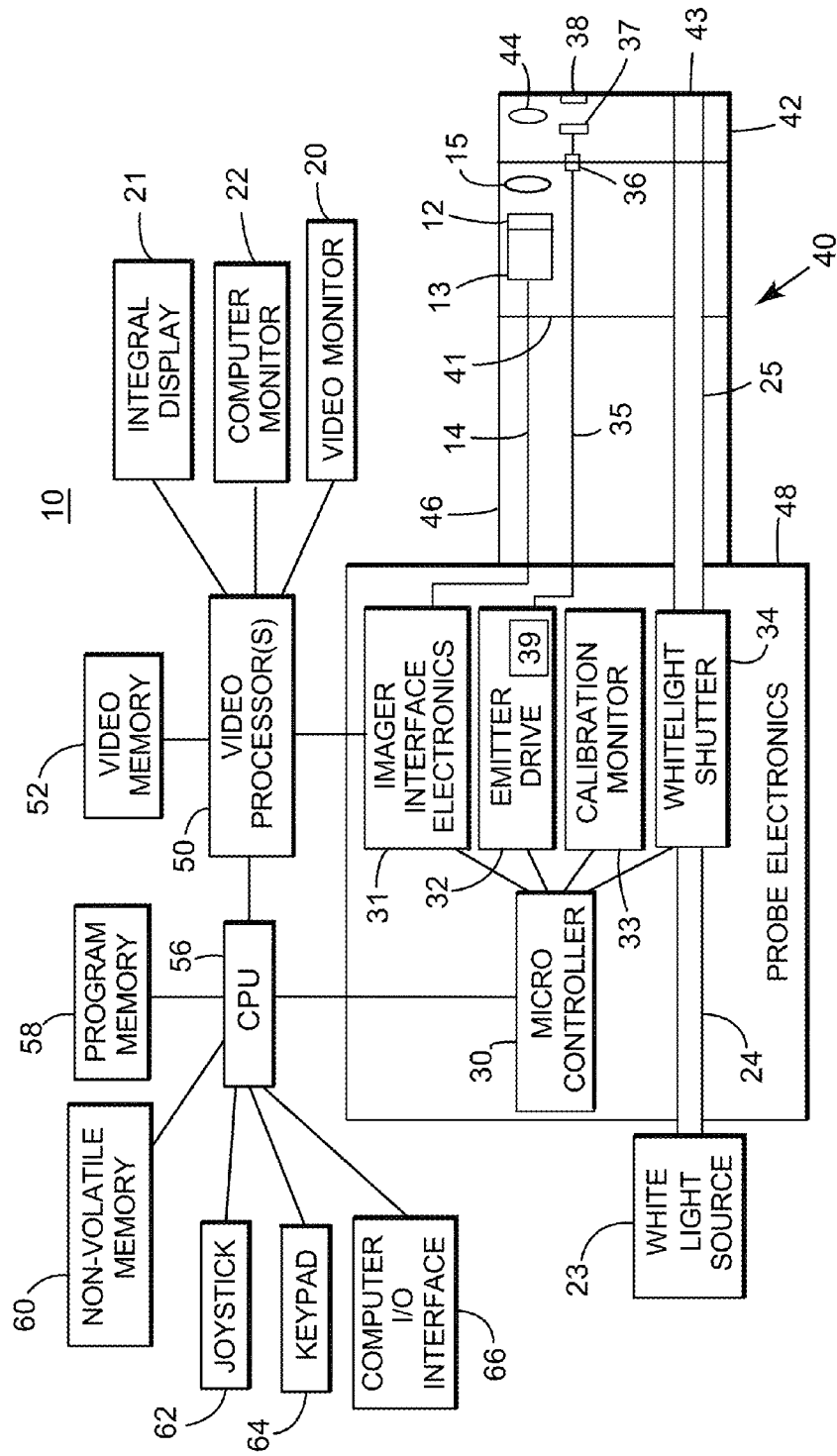
FIG. 1 is a schematic diagram of a exemplary probe (borescope/endoscope) system.

Illustrated in FIG. 1, an exemplary borescope/endoscope probe or system 10 is shown. An insertion tube 40 comprises elongated portion 46 and detachable distal tip 42. Elongated portion 46 comprises a main long, flexible portion, a bending neck, and a camera head. Delineation line 41 shows where the camera head starts on elongated portion 46. The camera head of elongated portion 46 typically includes at least imager 12, electronics 13, and probe optics 15. Detachable distal tip 42 typically attaches to the camera head of elongated portion 46, mentioned above. Detachable distal tip 42 contains viewing optics 44 which are used in combination with probe optics 15 to guide and focus light received from the surface or object (not shown) onto imager 12. The viewing optics 44 may optionally include relay optics such as a lens or fiber optic system to remote the camera head away from the distal tip 42.

Imager 12 may comprise, for example, a two-dimensional array of light-sensitive pixels that outputs a video signal in response to the light level sensed at each pixel. Imager 12 may comprise a charge-coupled device (CCD), complementary metal-oxide-semiconductor (CMOS) image sensor, or other devices of similar function. The video signal is buffered by electronics 13 and transferred to imager interface electronics 31 via signal line 14. Imager interface electronics 31 may include, for example, power supplies, a timing generator for generating imager clock signals, an analog front end for digitizing the imager video output signal, and a digital signal processor for processing the digitized imager video data into a more useful format for video processor 50.

Video processor 50 performs various functions not limited to image capture, image enhancement, graphical overly merging, and video format conversion and stores information relating to those functions in video memory 52. Video processor 50 may comprise field-programmable gate array (FPGA), digital signal processor (DSP), or other processing elements and provides information to and receives information from central processing unit (CPU) 56. The provided and received information may relate to commands, status information, video, still images, and/or graphical overlays. Video processor 50 also outputs signals to various monitors such as computer monitor 22, video monitor 20, and integral display 21.

When connected, each of computer monitor 22, video monitor 20, and/or integral display 21 typically display images of the object or surface under inspection, menus, cursors, and measurement results. Computer monitor 22 is typically an external computer type monitor. Similarly, video monitor 20 typically includes an external video monitor. Integral display 21 is integrated and built into probe or system 10 and typically comprises a liquid crystal display (LCD).

CPU 56 preferably uses both program memory 58 and non-volatile memory 60, which may include removable storage devices. CPU 56 may also use volatile memory such as RAM for program execution and temporary storage. A keypad 64 and joystick 62 convey user input to CPU 56 for such functions as menu selection, cursor movement, slider adjustment, and articulation control. Computer I/O interface 66 provides various computer interfaces to CPU 56 such as USB, Firewire, Ethernet, audio I/O, and wireless transceivers. Additional user I/O devices such as a keyboard or mouse may be connected to computer I/O interface 66 to provide user control. CPU 56 generates graphical overlay data for display, provides recall functions and system control, is configured to perform phase-shift analysis and measurement processing, and provides image, video, and audio storage.

Probe or system 10 further comprises contacts 36 that electrically couple elongated portion 46 to distal tip 42 through the camera head. Contacts 36 may be spring loaded and also provide electrical power from drive conductor 35 to light emitter module 37, which comprises a plurality of light emitters. Drive conductor 35 carries power from emitter drive 32 to the plurality of light emitters disposed in parallel on the distal end of insertion tube 40. Drive conductor 35 comprises one or more wires and may be incorporated with signal line 14 in a common outer jacket (not shown). Drive conductor 35 may also share conductors with signal line 14 and/or utilize the insertion tube 40 structure for carrying current. Emitter drive 32 includes, for example, an adjustable current source with a variable on time to compensate for light emitters with differing power capabilities and efficiencies. Emitter drive 32 also comprises brightness or fringe contrast determining function 39. Alternatively, video processor 50, discussed above, may include fringe contrast determining function 39.

The at least one light emitter module 37 on distal tip 42 comprises a plurality of light emitters and optionally other electronics for control/sequencing of light emitters, sensing temperature, and storage/retrieval of calibration data. The at least one light emitter module 37 may include a heat sink made of a ceramic or metal, for example, to reduce the temperature rise of the plurality of light emitters. Light from the plurality of light emitters disposed on distal tip 42 is passed through at least one intensity modulating element 38 to alter the distribution of light and project at least one structured-light pattern on the surface suitable for phase-shift analysis. A fringe set comprises a structured-light pattern projected when one light emitter group of at least one of the plurality of light emitters is emitting light. Light from the plurality of light emitters is passed through the at least one intensity modulating element 38 to project a plurality of fringe sets onto the surface.

The probe operates in measurement mode when the at least one of the plurality of fringe sets is projected onto the surface. During measurement mode, light emitter module 37 is enabled and at least one digital image comprising a structured-light pattern on the surface is captured. Phase-shift analysis is may be performed directly on the at least one captured digital image. It may also be performed on data derived from the at least one captured digital image. For example, a luminance component derived from an YCrCb, RGB, or any other captured image format could be used. Thus, any reference to performing phase-shift analysis on an image made herein would include performing phase-shift analysis on the actual referenced image or on any data derived from the referenced image.

The probe operates in inspection mode when the at least one structured-light pattern is absent. During inspection mode, inspection light source 23 is enabled and outputs light from the distal end of insertion tube 40. The elements that produce and deliver light during inspection mode may collectively be referred to as an inspection light delivery system. In one embodiment, the inspection light delivery system comprises inspection light source 23, source fiber bundle 24, shutter mechanism 34, probe fiber bundle 25, and light passing element 43. In other embodiments, the inspection light delivery system may comprise very different elements such as, in the case of distally-located white LEDs, an LED drive circuit that can be disabled or provides an adjustable output current, wires for delivering power to the LEDs, the LEDs themselves, and a protective element to protect the LEDs. During measurement mode, the intensity of light output from the inspection light delivery system is automatically decreased to avoid reducing the contrast of the at least one structured-light pattern, for example.

Inspection light source 23 is typically a white light source, but may comprise any appropriate light source for a probe such as a mercury or metal halide arc lamp, halogen lamp, laser/phosphor system, or LED based light source which could be either proximally or distally located. When a fiber based light source is used, source fiber bundle 24 is included in probe or system 10. Source fiber bundle 24 comprises a non-coherent or semi-coherent fiber optic bundle and transmits light to shutter mechanism 34. Shutter mechanism 34 allows light output from the inspection light delivery system during inspection mode or regular inspection and blocks or otherwise inhibits light output from the inspection light delivery system during measurement mode or measurement pattern projection. Shutter mechanism 34 includes, for example, a solenoid or motor driven mechanical shutter or an electric light source disabler. The location of shutter mechanism 34 can vary based on its implementation. When shutter mechanism 34 allows light to pass, probe fiber bundle 25 delivers light to the surface or inspection site via light passing element 43. Probe fiber bundle 25 comprises a non-coherent fiber optic bundle. Light passing element 43 comprises a glass cane, formed fibers, and/or distribution control features such as lenses or a diffuser.

The previously discussed imager interface electronics 31, emitter drive 32, and shutter mechanism 34 are included in the probe electronics 48. Probe electronics 48 may be physically separated from a main control unit or CPU 56 to provide more local control over probe-related operations. Probe electronics 48 further comprise calibration memory 33. Calibration memory 33 stores information relating to the optical system of distal tip 42 and/or elongated portion 46 such as magnification data, optical distortion data, and pattern projection geometry data.

Microcontroller 30, also included in probe electronics 48, communicates with imager interface electronics 31 to determine and set gain and exposure settings, controls emitter drive 32 circuitry, stores and reads calibration data from the calibration memory 33, controls shutter mechanism 34, and communicates with CPU 56.

Referring back to distal tip 42, the elements shown in distal tip 42 could alternatively be located on elongated portion 46. These elements include viewing optics 44, at least one light emitter module 37, at least one intensity modulating element 38, and light passing element 43, discussed above. In addition, the at least one light emitter module 37 comprising a plurality of light emitters could be fixedly attached to insertion tube 40 while the at least one intensity-modulating element 38 is disposed on distal tip 42. In this case, precise and repeatable alignment between distal tip 42 and elongated portion 46 is required, but it is advantageous because allows different fields of view while eliminating the need for contacts between elongated portion 46 and distal tip 42.

Mentioned above, a structured-light pattern is created on the surface by passing light through at least one intensity-modulating element 38, which alters the distribution of light. The structured-light pattern preferably comprises parallel light and dark lines comprising sinusoidal intensity profiles. Line patterns having square, trapezoidal, triangular, or other profiles may be projected on the surface as well when used with appropriate phase-shift analysis to determine phase of the pattern. The pattern may also comprise other than straight, parallel lines. For example, curved lines, wavy lines, zigzagging lines, or other such patterns may be used with appropriate analysis.

Figure 3:
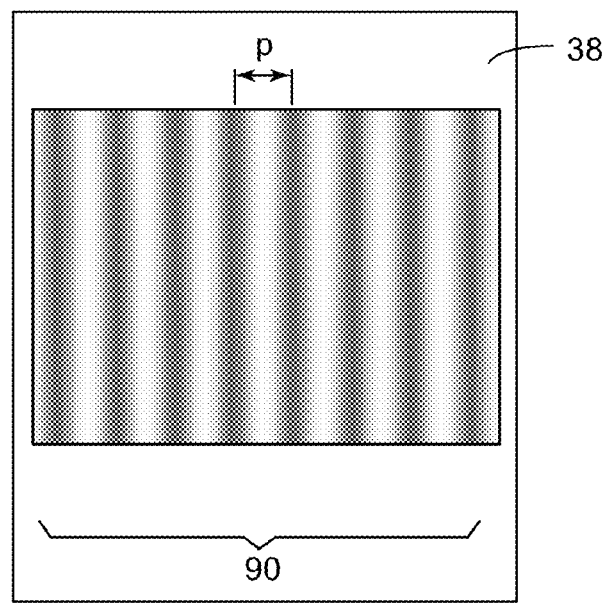
FIG. 3 is a top view of an exemplary intensity modulating element including a line grating.

In one embodiment, the at least one intensity modulating element 38 comprises line grating 90, shown in FIG. 3. In addition, the at least one light emitter module comprises a plurality of light emitters. Particularly, the at least one light emitter module comprises LEDs or an LED array.

A fringe set comprises a structured-light pattern projected when one light emitter group of at least one of the plurality of light emitters is emitting light. The plurality of light emitters of light emitter module 37 are positioned such that the structured-light pattern projected when one group of at least one light emitter is emitting exhibits a spatial or phase-shift relative to the structured-light patterns projected when other groups of at least one light emitter are emitting. In other words, the structured-light pattern of one fringe set exhibits a spatial or phase-shift relative to the structured-light patterns of other fringe sets.

Figure 2:
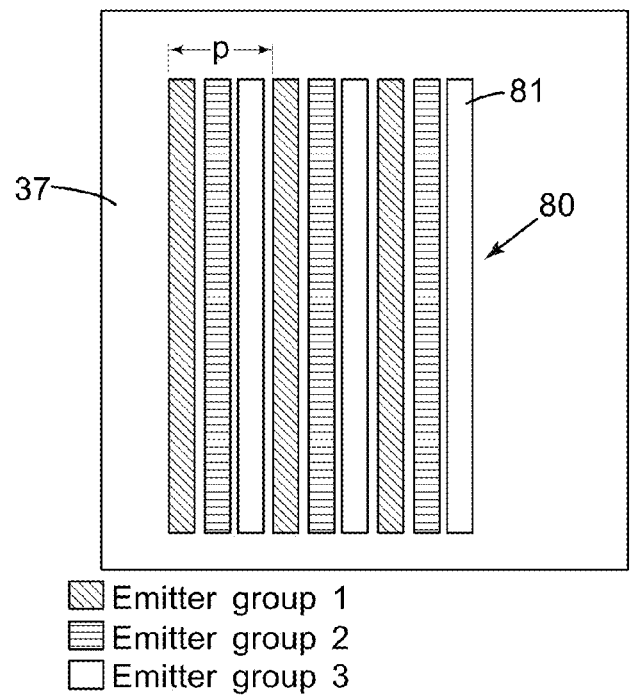
FIG. 2 is top view of an exemplary light-emitting diode (LED) array on a light emitter module made using elongated die.

FIG. 2 illustrates an exemplary case when LED array 80 is made using elongated die. In FIG. 2, line grating 90 (not shown here, but shown in FIG. 3) has a grating period p. Each light emitter 81 has a width less than ⅓ of the grating period p, and each light emitter 81 is lined up adjacent to each other with a center-to-center spacing of p/3. In this configuration, the line pattern projected when one light emitter 81 is emitting has a spatial or phase-shift of approximately ⅓ of the line period or 120° relative to the line pattern projected when the adjacent light emitter 81 is emitting. Exemplary emitting area dimensions for each light emitter 81 used with an 8 cycle/mm grating period p may be 35 μm×500 μm.

Alternatively, an effective phase-shift of 120° can be achieved with configurations in which the light emitter 81 spacing is other than ⅓ of the grating period. For example, with an light emitter 81 spacing of ⅔ of the grating period, the light pattern projected when one light emitter 81 is emitting may have a phase-shift of 240° relative to the line pattern projected when the adjacent light emitter 81 is emitting. In this configuration, each light emitter 81 has width less than ⅔ of the grating period p, and each light emitter 81 is lined up adjacent to each other with a center-to-center spacing of 2p/3. Because multiple lines are projected each having a 0 to 360° phase range, the 240° phase-shift is equivalent to a 120° phase-shift. To generalize, by positioning light emitters 81 with a center-to-center spacing of approximately p/3 of the grating period where p is an integer that is not a multiple of 3, the light pattern projected when one light emitter 81 is emitting may have an effective phase-shift of approximately 120° relative to the line pattern projected when the adjacent light emitter 81 is emitting.

Referring back to FIG. 2, multiple light emitters 81 are spaced apart by one grating period to create three separate light emitter groups. For clarification only, the light emitters 81 that comprise each of the three light emitter groups in FIG. 2 are indicated with a different pattern. LED array 80 comprises individual light emitters 81 of the same color. However, the color of light emitters 81 comprising one light emitter group can differ from the color of the light emitters 81 comprising other light emitter groups.

A plurality of light emitters 81 comprising each light emitter group are spaced apart along the axis perpendicular to the light emitters 81 and to the lines on the line grating by a distance approximately equal to an integer number of periods of the line grating. As a result, when the plurality of light emitters 81 comprising one light emitter group are simultaneously emitting light, the structured-light patterns produced by each of the multiple light emitters 81 sum together. This forms a brighter line pattern than would be generated by a single light emitter element. Increasing the light emitter width can increase brightness, but the line grating period must increase proportionally causing proportionally higher sensitivity to image noise. By using a plurality of narrow light emitters 81 as described, the pattern brightness can be increased without increasing the line grating period.

Emitter drive 32 of FIG. 1 comprises a brightness or fringe contrast determining function 39 to determine whether one light emitter 81 or multiple light emitters 81 should be enabled for each light emitter group. Because the light from the light emitters 81 is not collimated, the projected fringe sets expand as distance from the line grating increases. When multiple light emitters 81 of a light emitter group are simultaneously emitting, the individual fringe sets are offset by a constant distance (one grating period p as shown in the exemplary cases of FIGS. 2 and 3) rather than a constant phase, so their phases become more aligned as they expand. This results in progressively higher contrast as distance from the grating increases. Thus, when measuring a surface where more intensity is needed to achieve low image noise, multiple light emitters 81 from the same fringe set can be simultaneously turned on to provide more brightness at high contrast. However, at close distances, the sinusoidal intensities are not phase aligned and fringe set contrast decreases. Also, less intensity is needed at close distances; so when viewing a closer surface, one light emitter 81 can be turned on to achieve adequate intensity and high contrast.

Depending on the evaluation from brightness or fringe contrast determining function 39, one light emitter 81 or multiple light emitters 81 in each light emitter group are enabled for each fringe set. In one embodiment, drive conductor 35 comprises one or more drive wires (not shown) per LED. Brightness or fringe contrast determining function 39 selectively transmits current through specific drive wires of drive conductor 35 to light an appropriate number of LEDs per fringe set.

Alternatively, brightness or fringe contrast determining function 39 can be located separately from emitter drive 32 and may comprise, for example, an analog detection circuit or video processor. With that assembly, one drive wire of drive conductor 35 connects emitter drive 32 to light emitter module 37, and one or more control wires (not shown) controlled by brightness or fringe contrast determining function 39 are also connected to light emitter module 37. A circuit (not shown) included on light emitter module 37 can selectively connect one or multiple LEDs to the drive wire in response to signals on the control wire(s).

Through the use of multiple light emitters 81 per fringe set and brightness or fringe contrast determining function 39, LED array 80 offers adequate brightness and contrast during image capture and measurement. LED array 80 also offers consistent, uniform illumination, no speckling, and fast switching between fringe sets. Fast switching allows fringe set images to be captured in sequential frames, which reduces the likelihood of motion between image capture times. For at least these reasons, LED arrays are practical in this configuration. However, any light emitting source(s) offering the qualities mentioned above are sufficient for use in probe or system 10. Other such light sources include, but are not limited to, organic LEDs, plasma elements, fiber coupled lasers, and laser arrays.

Figure 4:
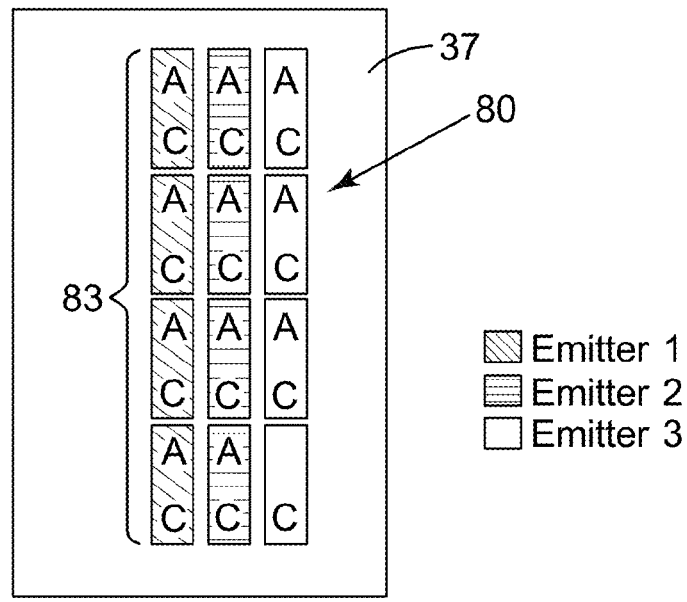
FIG. 4 is a top view of an exemplary LED array on a light emitter module where each light emitter comprises four LEDs connected in series.
Figure 5:
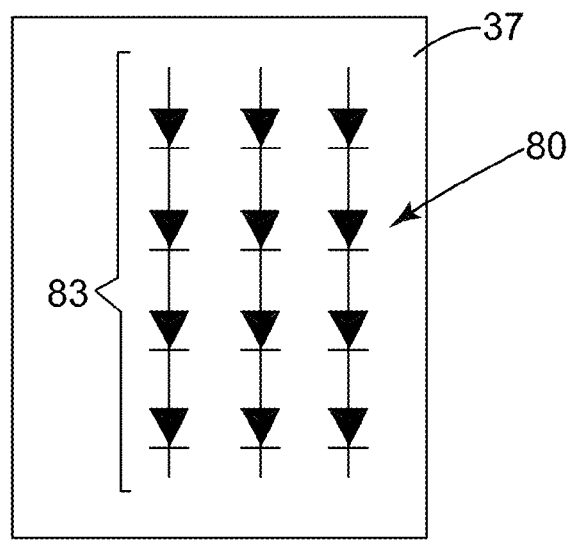
FIG. 5 is a top view of the exemplary LED array of FIG. 4 illustrating the series connection.

In another embodiment, LED array 80 is made using multiple series LEDs that comprise one light emitter 81 of a light emitter group. A light emitter 81 in this configuration may also be referred to as a string. FIG. 4 illustrates an exemplary case when each light emitter or string 83 comprises 4 LEDs connected in series. FIG. 5 illustrates the series connection. Each light emitter or string 83 would be offset by approximately p/3 periods, where p is an integer that is not a multiple of 3. Similar to FIG. 2, for clarification only, the plurality of LEDs that comprise one light emitter 81 of a light emitter group are indicated with a different pattern. Each of the plurality of light emitters 81 may comprise a series string of at least two LEDs. In FIG. 4, three strings are shown comprising four LEDs each, each string comprising its own light emitter group. However, as described in relation to FIG. 2, a light emitter group may comprise a plurality of light emitters 81 or strings as well.

LED output is typically proportional to drive current. But, supplying high currents to distally-located LEDs using small wires is highly inefficient. By using multiple LEDs connected in series to comprise one light emitter or string 83, less current is required to achieve a given combined LED output level. For example, series strings of 4 LEDs as shown in FIG. 4 can achieve the same output as single LEDs using $\frac{1}{4}^{th}$ of the current.

Figure 6:
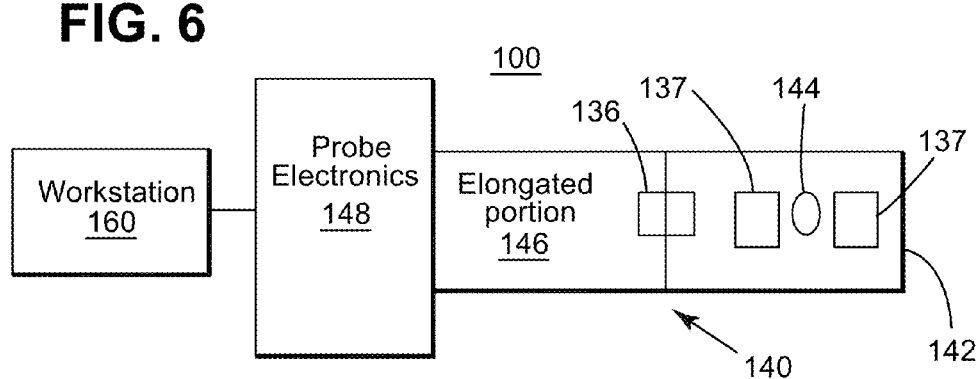
FIG. 6 is a generalized schematic diagram of an exemplary probe system.

Referring now to FIG. 6, borescope/endoscope probe or system 100 is shown generally in accordance with another embodiment. Probe or system 100 comprises insertion tube 140, probe electronics 148, and workstation 160. Workstation 160 comprises similar elements to those connected to probe electronics 48 described in detail and shown FIG. 1. Probe or system 100 as a whole also comprises similar elements and operates in a similar manner as probe or system 10 of FIG. 1.

Insertion tube 140 comprises elongated portion 146 and detachable distal tip 142. Detachable distal tip 142 comprises two light emitter modules 137, forward viewing optics 144, and contacts 136. Contacts 136 provide power to distal tip 142, electrically couple elongated portion 146 to distal tip 142, and may be spring loaded. Insertion tube 140 may also comprise at least one intensity modulating area (not shown).

Figure 7:
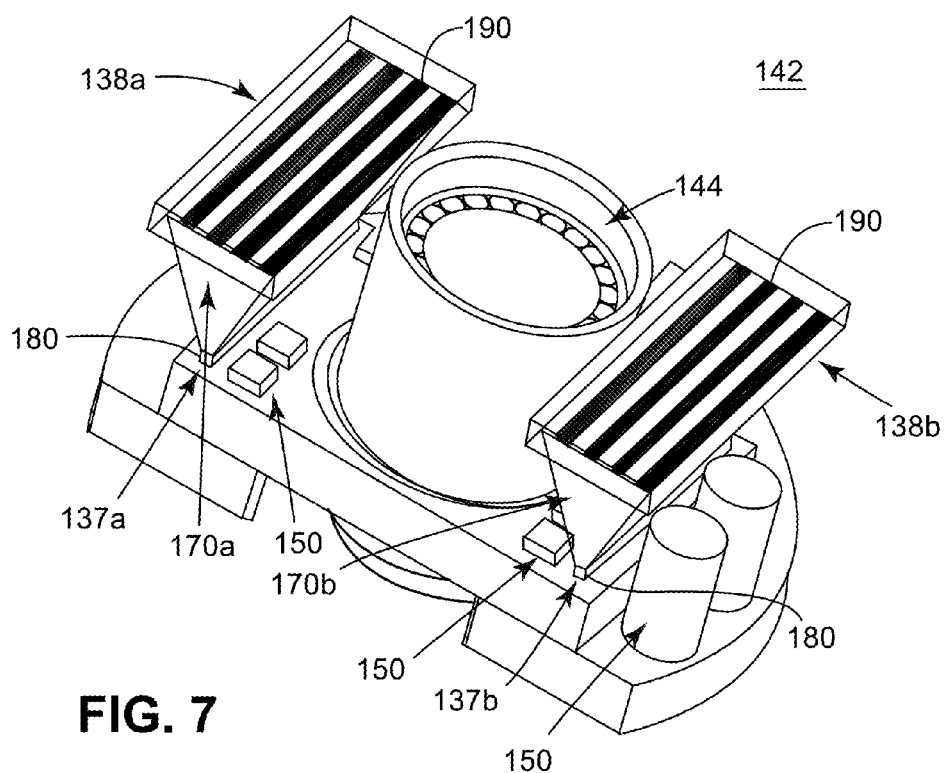
FIG. 7 is a perspective view of an exemplary embodiment of a detachable tip as shown in FIG. 6.

Referring now to FIG. 7, an exemplary embodiment of distal tip 142 of FIG. 6 is shown. Like FIG. 6, two light emitter modules 137 comprising a plurality of light emitters are positioned on each side of forward viewing optics 144. The plurality of light emitters positioned on one side of viewing optics 144 comprises first light emitter module 137a, and the plurality of light emitters positioned on the other side of viewing optics 144 comprises second light emitter module 137b. In addition, intensity modulating element 138 comprises two intensity modulating areas 138a and 138b, one intensity modulating area positioned on each side of forward viewing optics 144. Light from first light emitter module 137a is passed via path 170a through intensity modulating area 138a, which forms a first projection set, and light from second emitting module 137b is passed via path 170b through intensity modulating area 138b, which forms a second projection set. Intensity modulating element 138 comprises line grating 190, which alters the distribution of light and creates a structured-light pattern on the surface compatible with phase-shift analysis.

An imager (not shown) obtains a first image set and a second image set. The first image set comprises at least one image of a projection onto the surface of at least one of the plurality of fringe sets of the first projection set, and the second image set comprises at least one image of a projection onto the surface of at least one of the plurality of fringe sets of the second projection set.

First light emitter module 137a associated with first intensity modulating area 138a is positioned on one side of viewing optics 144, and second light emitter module 137b associated with second intensity modulating area 138b is positioned on the other side of viewing optics 144 such that the at least one structured-light pattern reflected from the surface passes through viewing optics 144 to reach the imager (not shown).

The two light emitter modules 137 each comprise an elongated LED array 180, which in turn comprises at least three light emitters. Alternatively, the two light emitter modules 137 may each comprise a plurality of light emitters, each of the plurality of light emitters comprising a series string of at least two LEDs. A light passing element (not shown), which delivers light from an inspection light source 23 (FIG. 1) to the surface may also be included in distal tip 142. Optional circuitry 150 located on distal tip 142 may control sequencing of the LEDs, select between single and multiple LEDs, sense temperature, and store/retrieve calibration data. The optional circuitry 150 could be managed by the CPU 56 or microcontroller 30 shown in FIG. 1.

In probe or system 100, the first projection set comprises a plurality of fringe sets and the second projection set comprises a plurality of fringe sets. The plurality of light emitters are positioned such that the structured-light pattern of one fringe set of the first projection set projected from one light emitter group of the first light emitter module exhibits a phase-shift relative to the structured-light patterns of the other fringe sets of the first projection set projected from the other light emitter groups of the first light emitter module. Similarly, the structured-light pattern of one fringe set of the second projection set projected from one light emitter group of the second light emitter module exhibits a phase-shift relative to the structured-light patterns of the other fringe sets of the second projection set projected from the other light emitter groups of the second light emitter module.

The plurality of light emitters are positioned such that the structured-light pattern of one fringe set of the first projection set exhibits a spatial or phase-shift relative to the structured-light patterns of other fringe sets of the first projection set. Similarly, the structured-light pattern of one fringe set of the second projection set exhibits a spatial or phase-shift relative to the structured-light patterns of other fringe sets of the second projection set.

In one embodiment, the first light emitter module comprises three light emitter groups and the second light emitter module comprises three light emitter groups. Therefore, three fringe sets comprising the first projection set are produced from one side of viewing optics 144 and three fringe sets comprising the second projection set are produced from the other side of viewing optics 144. Therefore, probe or system 100 can project a total of six fringe sets, three fringe sets from each side of the FOV. In order to improve brightness and contrast, light emitter modules 137a and 137b may include more than three LEDs along with a brightness determining function as described in detail above. Furthermore, the plurality of light emitters of light emitter modules 137a and 137b may each include a series string of at least two LEDs.

The accuracy of a system employing structured-light projection and phase-shift analysis is largely determined by its baseline spacing. In the case of a typical system wherein the absolute phase of a fringe set combined with its position in the FOV are used to determine absolute object distance, the baseline spacing is the distance between the projection origin and the camera field of view origin. In this embodiment, wherein the difference between the absolute phases of the two separate fringe sets is used to determine absolute object distance, the baseline spacing is the distance between light emitter modules 137a and 137b. Thus, accuracy is improved when the distance between the two light emitter modules 137a and 137b is larger than the distance between the viewing optics 144 and a single light emitter module 137. As mechanical constraints in small-diameter probes make it difficult to substantially offset the viewing optics 144 from the center of the insertion tube 140, the described embodiment employing two light emitter modules 137a and 137b can generally achieve a larger baseline spacing than could be achieved with a single light emitter module 137 in a forward-viewing system.

In addition, variability in the positioning of the distal tip 142 on the insertion tube causes the projections originating from the tip to shift relative to the FOV. If object distance is computed using absolute phase combined with position in the FOV, this shift causes error in the computed object distance. In this embodiment, such error is eliminated because the absolute phase difference is not affected by positioning of the tip on the insertion tube. In an alternative approach, the two LED arrays may also be located on one side of the viewing optics with a large grating where the first projection set is offset from the viewing optics by slightly more than the second projection set.

In some applications, it is desirable to obtain a view in a direction perpendicular to the probe axis, referred to as a side view. To obtain such a view, distal tip 142 may be replaced with a detachable side-viewing tip 242 (FIGS. 8 and 9) comprising elements such as a side-view prism 210 through which the plurality of fringe sets reflected from the surface pass through viewing optics 244 to reach the imager (not shown).

Figure 8A:
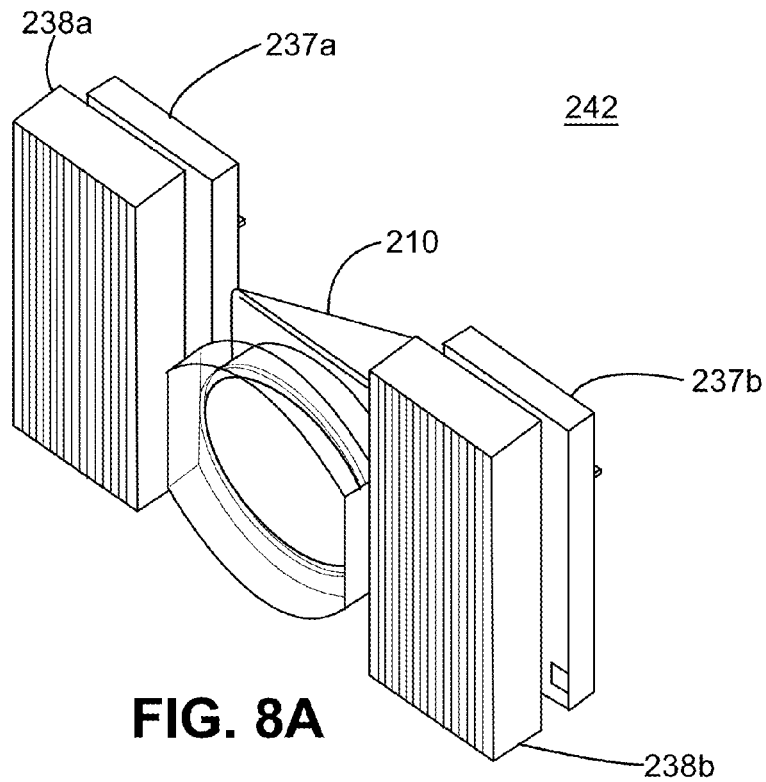
FIG. 8A is a perspective view of an exemplary embodiment of a detachable side-viewing tip.
Figure 8B:
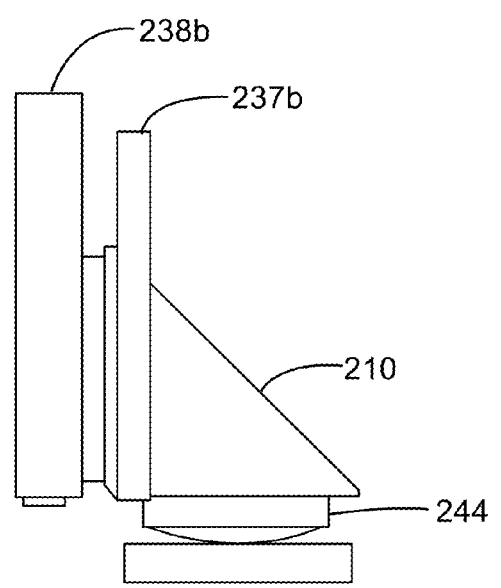
FIG. 8B is a side view of the exemplary detachable side-viewing tip of FIG. 8A.

FIGS. 8A and 8B show an exemplary embodiment of side-viewing tip 242. Seen in FIG. 8A, the plurality of light emitters are positioned to emit light in a direction substantially perpendicular to the axis of the probe. In this case, light emitter modules 237a and 237b are disposed on each side of side-view prism 210 and rotated 90° (relative to the position of the plurality of light emitter modules shown in FIG. 7) to direct the plurality of fringe sets to the side. Specifically, light emitter module 237a is disposed on one side of side-view prism 210, and light emitter module 237b is disposed on the other side of side-view prism 210. Furthermore, intensity-modulating area 238a is disposed on one side of side-view prism 210, and intensity-modulating area 237b is disposed on the other side of side-view prism 210 such that light emitted from light emitter module 237a passes through intensity modulating area 238a and light emitted from light emitter module 237b passes through intensity-modulating area 238b. FIG. 8B shows a side view of side-viewing tip 242.

Figure 9A:
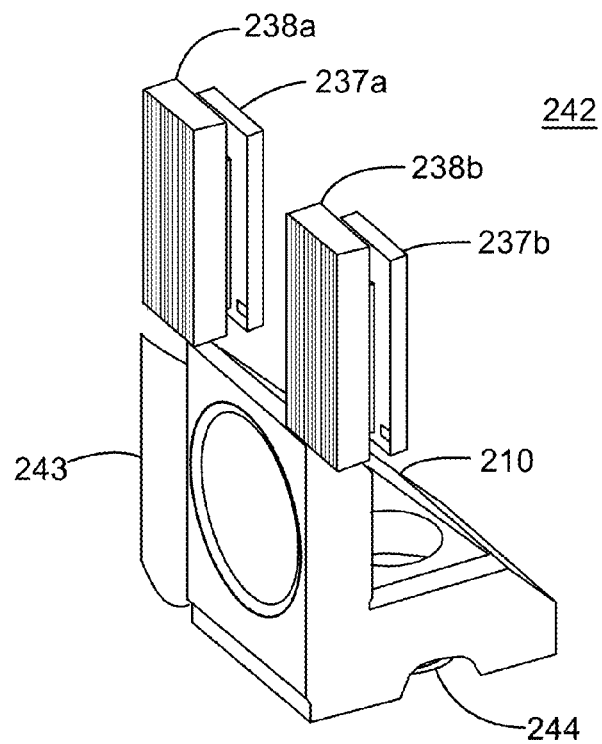
FIG. 9A is a perspective view of another exemplary embodiment of a detachable side-viewing tip.
Figure 9B:
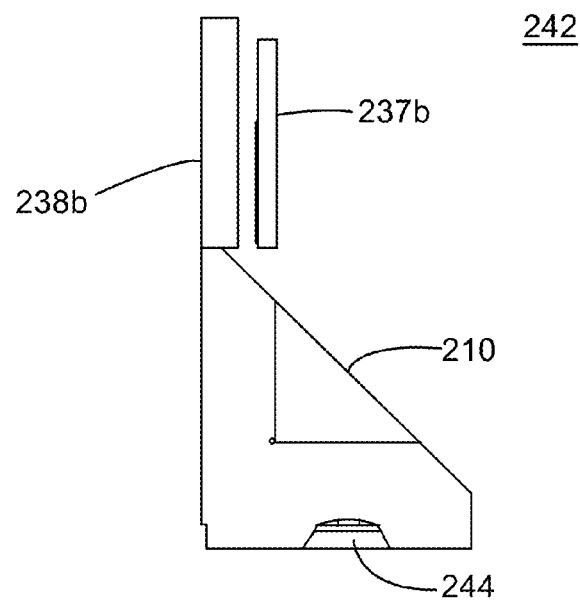
FIG. 9B is a side view of the exemplary detachable side-viewing tip of FIG. 9A.

In an alternative exemplary embodiment, shown in FIGS. 9A and 9B, light emitter modules 237a and 237b and intensity-modulating areas 238a and 238b are disposed above the top edge of side-view prism 210 and oriented perpendicularly to the top edge of side-view prism 210. Light emitter modules 237a and 237b are positioned to emit light in a direction substantially perpendicular to the axis of the probe. FIG. 9A shows light passing element 243 located on one side of side-view prism 210 to direct the light from the inspection light source (not shown) to the side. FIG. 9B shows a side view of side-viewing tip 242 in accordance with this exemplary embodiment.

Alternatively, the light emitter modules and intensity-modulating areas may be oriented parallel to the top edge of the prism. With that orientation, one light emitter module and intensity-modulating area may be disposed just above the top edge of the side-view prism while the other light emitter module and intensity-modulating area may be spaced more distally, further above the prism away from the imager. This way, the detachable side-viewing tip can be made longer to achieve a larger spacing between the light emitter modules without increasing the diameter of the insertion tube.

Figure 10:
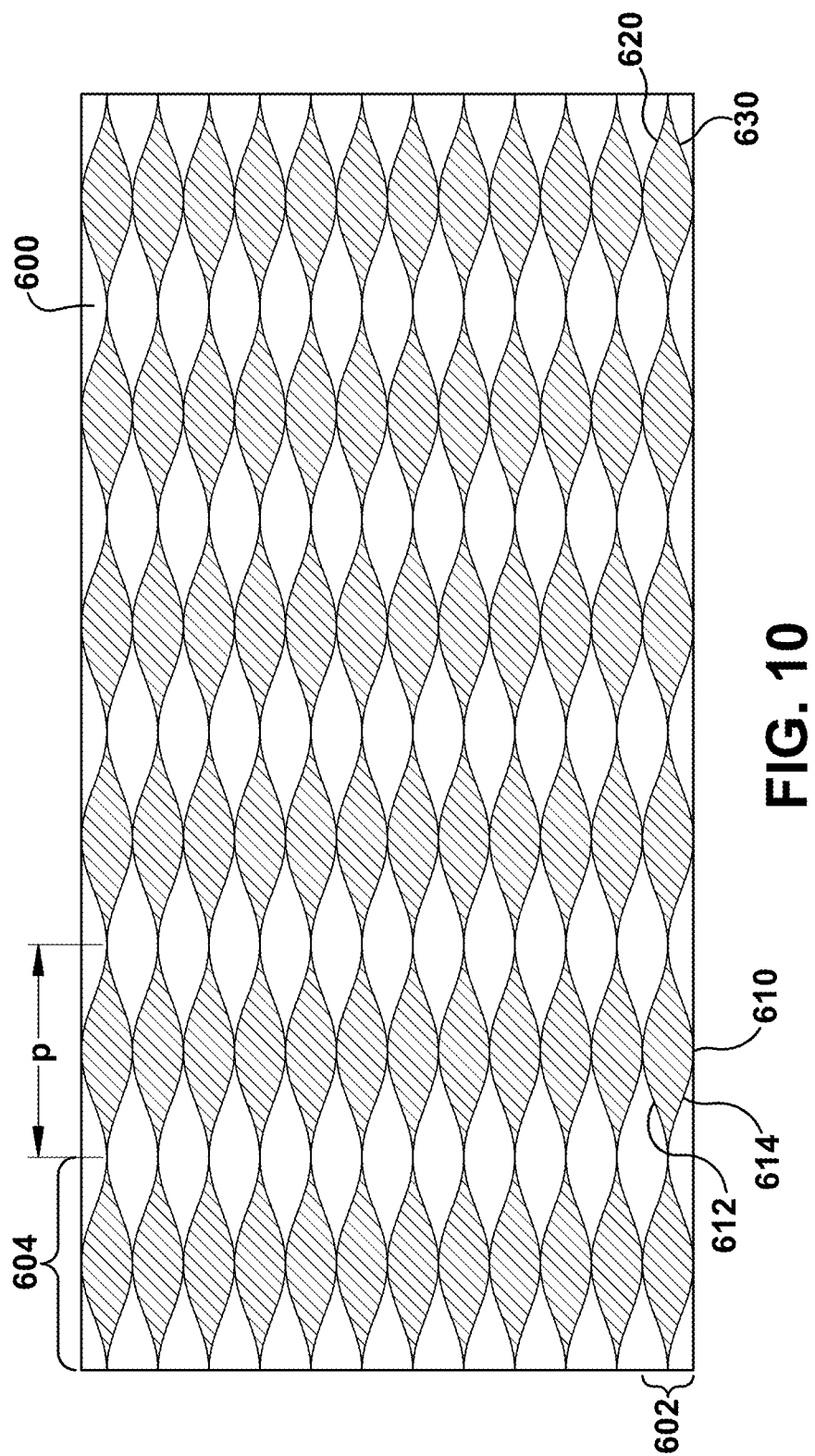
FIG. 10 is a top view of another exemplary intensity modulating element.

FIG. 10 is a top view of another exemplary intensity modulating element 600. The intensity modulating element 600 has plurality of columns 604 of a plurality of grating elements 610 having a grating period (p), wherein the plurality of columns 604 of the plurality of grating elements 610 are parallel to the plurality of light emitters 81 (see FIG. 2). In one embodiment, a first continuous sinusoidal pattern 620 (e.g., cosine, sine) extending perpendicular to the plurality of light emitters 81 forms the top side 612 of each of the plurality of grating elements 610, while a second continuous sinusoidal pattern 630 extending perpendicular to the plurality of light emitters 81 forms the bottom side 614 of each of the plurality of grating elements 610. The second continuous sinusoidal pattern 630 opposes and is the mirror image of the first continuous sinusoidal pattern 620. Each of the grating elements 610 extend for one grating period (p). The plurality of grating elements 610 can form a plurality of rows 602 of grating elements 610 extending for several grating periods (p) of the first continuous sinusoidal pattern 620 perpendicular to the plurality of light emitters 81.

Figure 11:
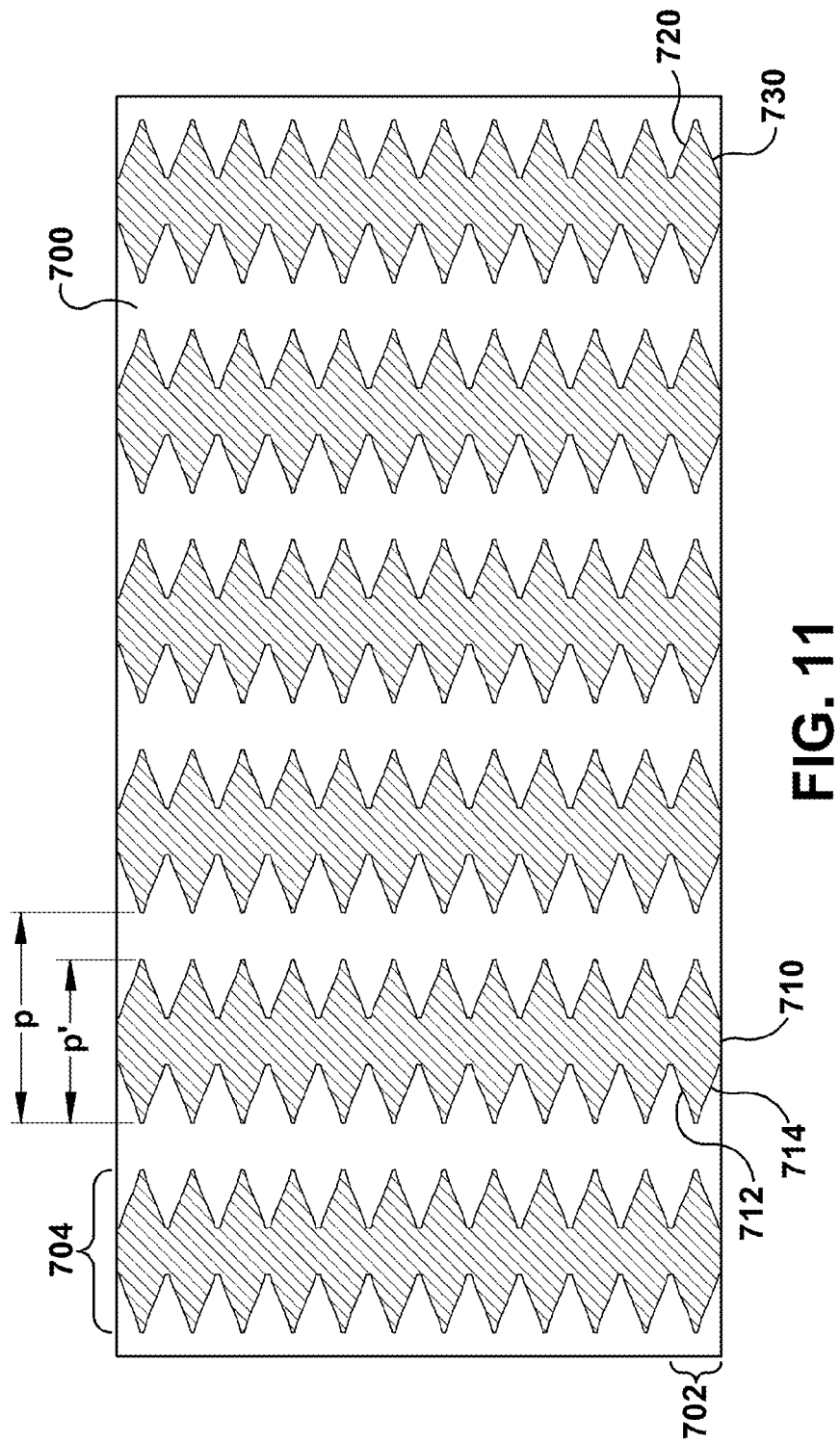
FIG. 11 is a top view of yet another exemplary intensity modulating element.
Figure 12:
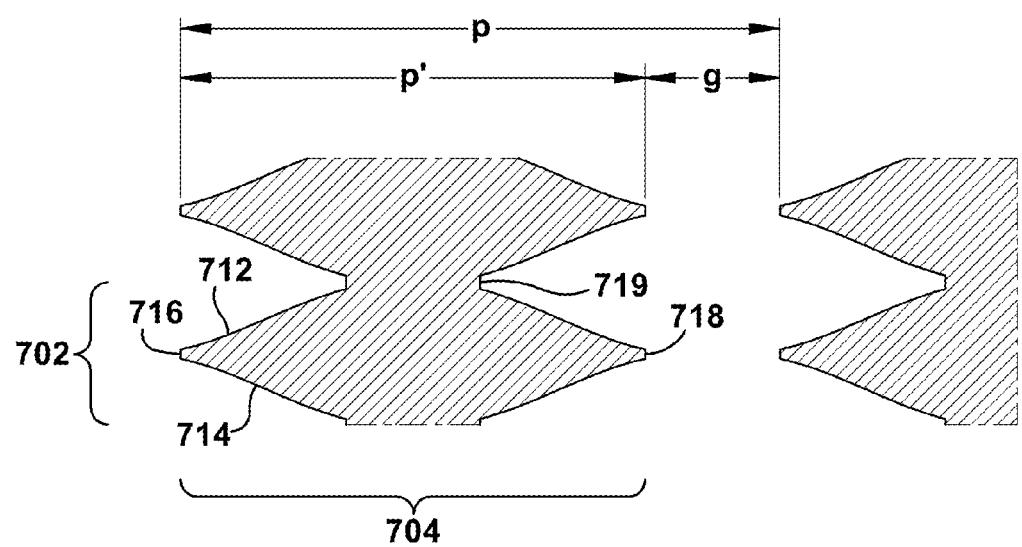
FIG. 12 is an enlarged view of the exemplary intensity modulating element as shown in FIG. 11.

FIG. 11 is a top view of yet another exemplary intensity modulating element 700. FIG. 12 is an enlarged view of the exemplary intensity modulating element 700 as shown in FIG. 11. The intensity modulating element 700 has plurality of columns 704 of a plurality of grating elements 710 having a grating period (p), wherein the plurality of columns 704 of the plurality of grating elements 710 are parallel to the plurality of light emitters 81 (see FIG. 2). In one embodiment, a first intermittent sinusoidal pattern 720 extending perpendicular to the plurality of light emitters 81 forms the top side 712 of each of the plurality of grating elements 710, while a second intermittent sinusoidal pattern 730 extending perpendicular to the plurality of light emitters 81 forms the bottom side 714 of each of the plurality of grating elements 710. The second intermittent sinusoidal pattern 730 opposes and is the mirror image of the first intermittent sinusoidal pattern 720. Each of the grating elements 710 extend for a portion (p') of one grating period (p). The portion (p') of the grating period (p) can be defined to start at the left side 716 of the grating element 710 and end at the right side 718 of the grating element 710, truncating the first intermittent sinusoidal pattern 720 and the second intermittent sinusoidal pattern 730 to improve the contrast of the resulting structured-light pattern. The plurality of grating elements 710 can form a plurality of rows 702 of grating elements 710 extending for several grating periods (p) of the first intermittent sinusoidal pattern 720 perpendicular to the plurality of light emitters 81 with a gap (g) between the grating elements 710 in the row 702. Adjacent grating elements 710 in the columns 704 of grating elements 710 can be connected by a web 719 extending from the top side 712 of one grating element 710 to the bottom side 714 of an adjacent grating element 710.

Figure 13:
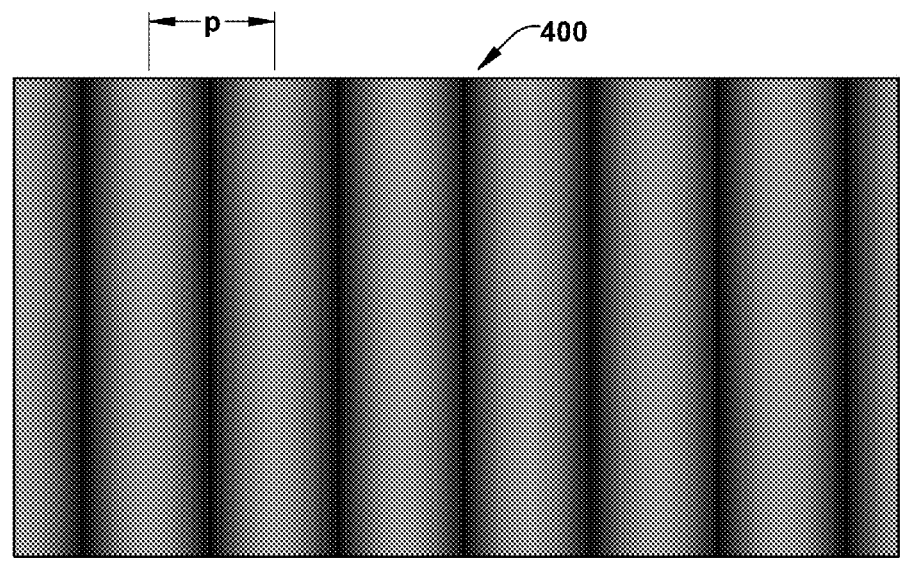
FIG. 13 is an exemplary image of a structured light pattern created by passing light through an intensity modulating element.
Figure 14:
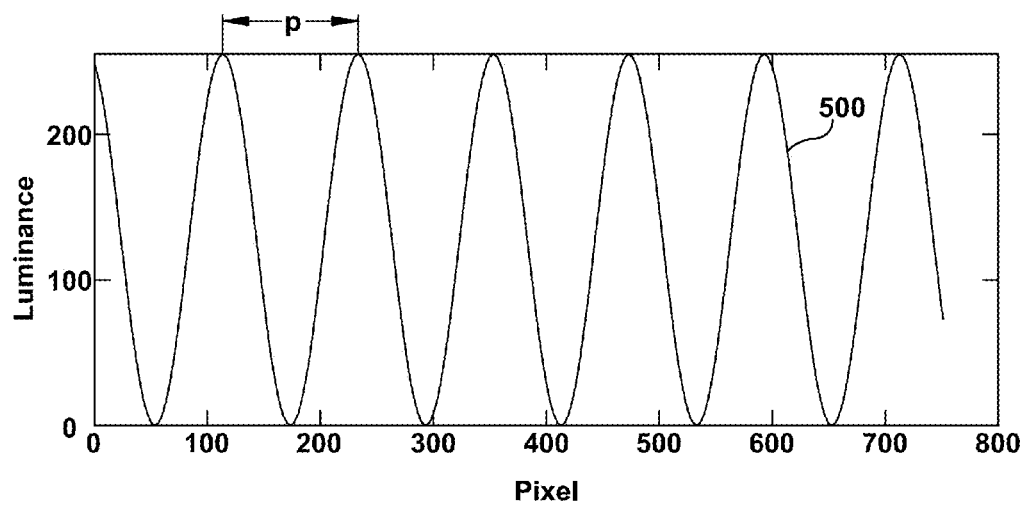
FIG. 14 is a plot of the sinusoidal intensity profile of an exemplary structured-light pattern.

A structured-light pattern 400, such as that shown in FIG. 13, is created on the surface by passing light through at least one intensity-modulating element 600, 700, which alters the distribution of light. The structured-light pattern 400 can comprise parallel light lines and dark lines comprising a sinusoidal intensity profile 500 in the direction perpendicular to the lines as shown in FIG. 14. As shown in FIGS. 13 and 14, the centers of the light lines have high luminance values and the centers of the dark lines have low or no luminance. With reference to the intensity modulating elements 600, 700 of FIGS. 10 and 11, the dark lines of the structured light pattern 400 shown in FIG. 11 and the zero luminance values of the sinusoidal intensity profile 500 shown in FIG. 12 are formed by the columns 604, 704 of grating elements 610, 710. The grating period (p) is shown as the distance from the center of one light line to the center of the next light line. It will be understood that the grating period can be defined to start (and end) at various points along the sinusoidal intensity profile 500.

In one embodiment, the length of the grating period (p) (e.g., 0.125 mm (0.0049 in.)) of the first sinusoidal pattern 620, 720 on the intensity modulating element 600, 700 can be at least two times the width of the light emitters 81 (as shown in FIG. 2) (e.g., 0.05 mm (0.00197 in.) to achieve good contrast while providing a reasonable number of light and dark lines in the captured images. In one embodiment, the left side 716 of the grating element 710 and the right side 718 of the grating element 710 can be 0.0020 mm (0.00008 in.) long (or thick), while the web 719 can also be 0.0020 mm (0.00008 in.) long (or thick). Reducing the length of the grating period (p) increases the number of light and dark lines and decreases the contrast of the image for a given light emitter 81 width. In one embodiment, the amplitude of first sinusoidal pattern 620, 720 can be much smaller (e.g., at least five times smaller) than the length of the light emitters 81 (as shown in FIG. 2) so that the amplitude of the individual sinusoids (0.015 mm (0.00118 in.) in the projected pattern is relatively small, minimizing degradation of the sinusoidal intensity profile 500 shown in FIG. 12, but is large enough to achieve good contrast with manufacturable feature sizes (e.g., greater than 0.001 mm (0.0000394 in.)). Higher pattern contrast can provide lower noise than lower pattern contrast. In one embodiment, the intensity modulating elements 600, 700 can have approximately 15 columns 604, 704 and approximately 100 rows 602, 702 of grating elements 610, 710.

In one embodiment, the substrate of the intensity modulating elements 600, 700 can be made of sapphire for maximum durability. In one embodiment, the grating elements 610, 710 are formed by photolithography on the intensity modulating elements 600, 700 using a coating that is highly absorptive of the wavelengths emitted by the light emitters 81 in order to minimize reflections. For example, if the light emitters 81 are emitting a red wavelength, a blue chrome that is highly absorptive (e.g., less than five percent at 750 nm) of the red wavelength can be used for the grating elements 610, 710. It will be understood that other coatings and colors can be used to provide high absorption of the wavelengths emitted by the light emitters 81 (e.g., black anodized). In one embodiment, the grating elements 610, 710 can be applied only on the front side (i.e., side of the intensity modulating element 600, 700 facing the light emitters 81), to avoid scratching or damage to the grating elements 610, 710 if located on the exposed back side of the intensity modulating element 600, 700. In another embodiment, the grating elements 610, 710 can be applied on only the back side of the intensity modulating element 600, 700, while in yet another embodiment, the grating elements 610, 710 can be applied to both the front side and the back side of the intensity modulating element 600, 700. In one embodiment, an anti-reflective coating can be applied on top of the grating elements 610, 710.

It will be understood that grating elements with non-sinusoidal patterns that approximate a sinusoidal pattern (e.g., a triangle pattern, a hexagon pattern) can also be used to produce a near sinusoidal intensity profile that can be compensated for during phase-shift analysis by the software.

Figure 15:
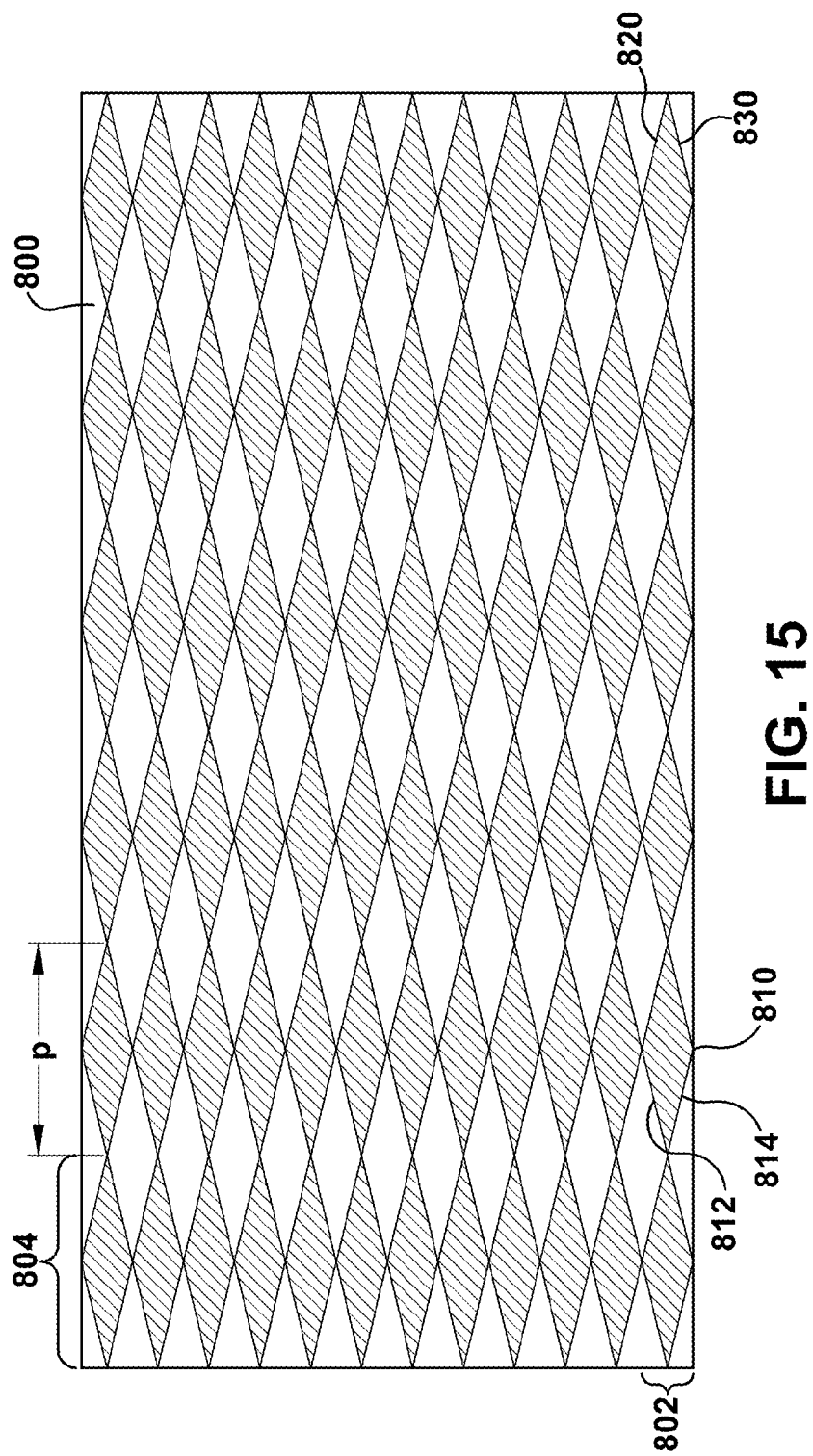
FIG. 15 is a top view of another exemplary intensity modulating element.

FIG. 15 is a top view of another exemplary intensity modulating element 800. The intensity modulating element 800 has plurality of columns 804 of a plurality of grating elements 810 having a grating period (p), wherein the plurality of columns 804 of the plurality of grating elements 810 are parallel to the plurality of light emitters 81 (see FIG. 2). In one embodiment, a first continuous triangle pattern 820 extending perpendicular to the plurality of light emitters 81 forms the top side 812 of each of the plurality of grating elements 810, while a second continuous triangle pattern 830 extending perpendicular to the plurality of light emitters 81 forms the bottom side 814 of each of the plurality of grating elements 810. The second continuous triangle pattern 830 opposes and is the mirror image of the first continuous triangle pattern 820. Each of the grating elements 810 extend for one grating period (p). The plurality of grating elements 810 can form a plurality of rows 802 of grating elements 810 extending for several grating periods (p) of the first continuous triangle pattern 820 perpendicular to the plurality of light emitters 81.

Figure 16:
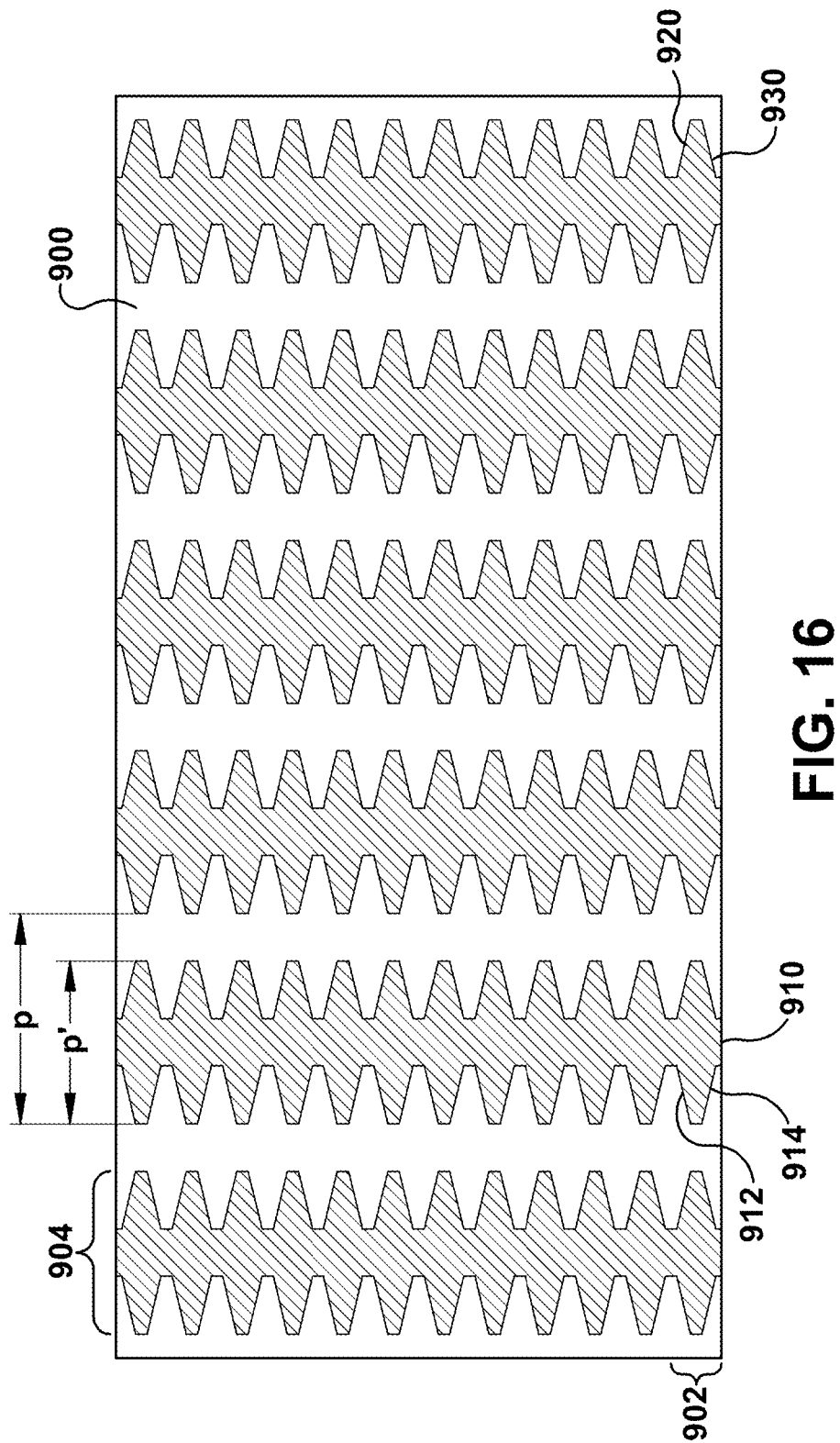
FIG. 16 is a top view of yet another exemplary intensity modulating element.
Figure 17:
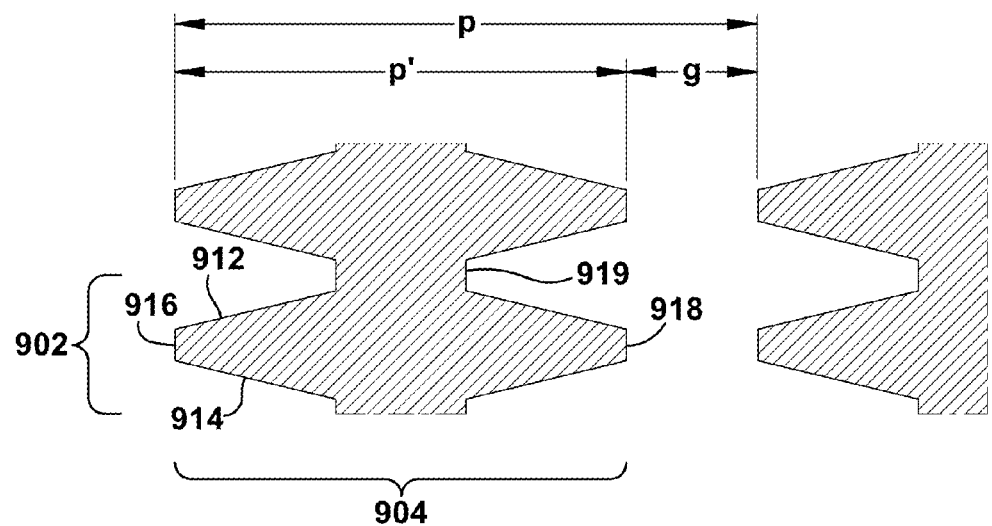
FIG. 17 is an enlarged view of the exemplary intensity modulating element as shown in FIG. 15.

FIG. 16 is a top view of yet another exemplary intensity modulating element 900. FIG. 17 is an enlarged view of the exemplary intensity modulating element 900 as shown in FIG. 16. The intensity modulating element 900 has plurality of columns 904 of a plurality of grating elements 910 having a grating period (p), wherein the plurality of columns 904 of the plurality of grating elements 910 are parallel to the plurality of light emitters 81 (see FIG. 2). In one embodiment, a first intermittent triangle pattern 920 extending perpendicular to the plurality of light emitters 81 forms the top side 912 of each of the plurality of grating elements 910, while a second intermittent triangle pattern 930 extending perpendicular to the plurality of light emitters 81 forms the bottom side 914 of each of the plurality of grating elements 910. The second intermittent triangle pattern 930 opposes and is the mirror image of the first intermittent triangle pattern 920. Each of the grating elements 910 extend for a portion (p') of one grating period (p). The portion (p') of the grating period (p) can be defined to start at the left side 916 of the grating element 910 and end at the right side 918 of the grating element 910, truncating the first intermittent triangle pattern 920 and the second intermittent triangle pattern 930 and forming a hexagon to improve the contrast of the resulting structured-light pattern. The plurality of grating elements 910 can form a plurality of rows 902 of grating elements 910 extending for several grating periods (p) of the first intermittent triangle pattern 920 perpendicular to the plurality of light emitters 81 with a gap (g) between the grating elements 910 in the row 902. Adjacent grating elements 910 in the columns 904 of grating elements 910 can be connected by a web 919 extending from the top side 912 of one grating element 910 to the bottom side 914 of an adjacent grating element 910.

The construction and arrangement of the fringe projection system and method, as described herein and shown in the appended figures, is illustrative only. Although only a few embodiments of the invention have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, orientations, etc.) without materially departing from the novel teachings and advantages of the subject matter recited in the appended claims. Accordingly, all such modifications are intended to be included within the scope of the invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the embodiments of the invention as expressed in the appended claims. Therefore, the technical scope of the present invention encompasses not only those embodiments described above, but also those that fall within the scope of the appended claims.

The construction and arrangement of the imager system and method, as described herein and shown in the appended figures, is illustrative only. Those skilled in the art will recognize that the imager system can include a conventional bore scope relay system, imaging bundle, or other means of removing the camera without deviating from the function of the described method. Although only a few embodiments of the invention have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, orientations, etc.) without materially departing from the novel teachings and advantages of the subject matter recited in the appended claims. Accordingly, all such modifications are intended to be included within the scope of the present invention as defined in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A probe comprising:
an insertion tube;
a plurality of light emitters disposed in parallel on the distal end of the insertion tube, wherein the plurality of light emitters are spaced apart along an axis perpendicular to the light emitters;
at least one intensity modulating element comprising a plurality of columns of a plurality of grating elements having a grating period, wherein the plurality of columns of the plurality of grating elements are parallel to the plurality of light emitters, and wherein the light from the plurality of light emitters is passed through the at least one intensity modulating element to project a plurality of fringe sets onto a surface, each of the plurality of fringe sets comprising a structured-light pattern projected when one emitter group of at least one of the plurality of light emitters is emitting;
an imager for obtaining at least one image of the surface; a processing unit that is configured to perform phase-shift analysis on the at least one image;
an inspection light delivery system which delivers light from an inspection light source to the surface;
wherein the inspection light delivery system outputs light from the distal end of the insertion tube during inspection mode;
wherein the intensity of light output from the inspection light delivery system is automatically decreased during measurement mode; and
wherein the probe operates in measurement mode when at least one of the plurality of fringe sets is projected onto the surface.

2. The probe of claim 1, wherein the plurality of grating elements comprise:

a first continuous sinusoidal pattern extending perpendicular to the plurality of light emitters forming the top side of each of the plurality of grating elements;

a second continuous sinusoidal pattern extending perpendicular to the plurality of light emitters forming the bottom side of each of the plurality of grating elements, wherein the second continuous sinusoidal pattern opposes and is the mirror image of the first continuous sinusoidal pattern; and wherein the plurality of grating elements form a plurality of rows of grating elements extending for several grating periods of the first continuous sinusoidal pattern perpendicular to the plurality of light emitters.

3. The probe of claim 1, wherein each of the plurality of grating elements comprise:

a first intermittent sinusoidal pattern extending perpendicular to the plurality of light emitters forming the top side of each of the plurality of grating elements;

a second intermittent sinusoidal pattern extending perpendicular to the plurality of light emitters forming the bottom side of each of the plurality of grating elements, wherein the second intermittent sinusoidal pattern opposes and is the mirror image of the first intermittent sinusoidal pattern;

a left side and a right side truncating the first intermittent sinusoidal pattern and the second intermittent sinusoidal pattern for each of the plurality of grating elements;

wherein the plurality of grating elements in the plurality of columns are connected by a web extending from the top side of one grating element to the bottom side of an adjacent grating element; and wherein the plurality of grating elements form a plurality of rows of grating elements extending for several grating periods of the first intermittent sinusoidal pattern perpendicular to the plurality of light emitters forming a gap between the left side of one grating element and the right side of an adjacent grating element in the row.

4. The probe of claim 1, wherein the plurality of grating elements comprise:

a first continuous triangle pattern extending perpendicular to the plurality of light emitters forming the top side of each of the plurality of grating elements;

a second continuous triangle pattern extending perpendicular to the plurality of light emitters forming the bottom side of each of the plurality of grating elements, wherein the second continuous triangle pattern opposes and is the mirror image of the first continuous triangle pattern; and wherein the plurality of grating elements form a plurality of rows of grating elements extending for several grating periods of the first continuous triangle pattern perpendicular to the plurality of light emitters.

5. The probe of claim 1, wherein each of the plurality of grating elements comprise:

a first intermittent triangle pattern extending perpendicular to the plurality of light emitters forming the top side of each of the plurality of grating elements;

a second intermittent triangle pattern extending perpendicular to the plurality of light emitters forming the bottom side of each of the plurality of grating elements, wherein the second intermittent triangle pattern opposes and is the mirror image of the first intermittent triangle pattern;

a left side and a right side truncating the first intermittent triangle pattern and the second intermittent triangle pattern for each of the plurality of grating elements;

wherein the plurality of grating elements in the plurality of columns are connected by a web extending from the top side of one grating element to the bottom side of an adjacent grating element; and wherein the plurality of grating elements form a plurality of rows of grating elements extending for several grating periods of the first intermittent triangle pattern perpendicular to the plurality of light emitters forming a gap between the left side of one grating element and the right side of an adjacent grating element in the row.

6. The probe of claim 1, wherein the structured-light pattern comprises parallel light and dark lines and wherein the parallel light and dark lines comprise sinusoidal intensity profiles.

7. The probe of claim 1, wherein the probe operates in measurement mode when at least one of the plurality of fringe sets is projected onto the surface.

8. The probe of claim 1, wherein the plurality of light emitters are positioned such that the structured-light pattern of one fringe set exhibits a phase-shift relative to the structured-light patterns of other fringe sets.

9. The probe of claim 1, wherein each of the plurality of light emitters comprises a string of at least two light emitting diodes.

10. The probe of claim 1, further comprising: a detachable distal tip comprising the at least one intensity-modulating element, wherein the plurality of light emitters are fixedly attached to the insertion tube.

11. An intensity modulating element for a probe having a plurality of light emitters disposed in parallel on the distal end of an insertion tube and spaced apart along an axis perpendicular to the light emitters, the intensity modulating element comprising:

a plurality of columns of a plurality of grating elements having a grating period, wherein the plurality of columns of the plurality of grating elements are parallel to the plurality of light emitters;

a first continuous sinusoidal pattern extending perpendicular to the plurality of light emitters forming the top side of each of the plurality of grating elements;

a second continuous sinusoidal pattern extending perpendicular to the plurality of light emitters forming the bottom side of each of the plurality of grating elements, wherein the second continuous sinusoidal pattern opposes and is the mirror image of the first continuous sinusoidal pattern; and wherein the plurality of grating elements form a plurality of rows of grating elements extending for several grating periods of the first continuous sinusoidal pattern perpendicular to the plurality of light emitters.

12. The intensity modulating element of claim 11, wherein the length of the grating period is at least two times greater than the width of the plurality of light emitters.

13. The intensity modulating element of claim 11, wherein the amplitude of the first continuous sinusoidal pattern is at least five times less than the length of the plurality of light emitters.

14. The intensity modulating element of claim 11, wherein a substrate of the intensity modulating element is made of sapphire.

15. The intensity modulating element of claim 11, wherein the plurality of grating elements are formed using a coating that is highly absorptive of the wavelengths emitted by the light emitters.

16. An intensity modulating element for a probe having a plurality of light emitters disposed in parallel on the distal end of an insertion tube and spaced apart along an axis perpendicular to the light emitters, the intensity modulating element comprising:
- a plurality of columns of a plurality of grating elements having a grating period, wherein the plurality of columns of the plurality of grating elements are parallel to the plurality of light emitters;
- a first intermittent sinusoidal pattern extending perpendicular to the plurality of light emitters forming the top side of each of the plurality of grating elements;
- a second intermittent sinusoidal pattern extending perpendicular to the plurality of light emitters forming the bottom side of each of the plurality of grating elements, wherein the second intermittent sinusoidal pattern opposes and is the mirror image of the first intermittent sinusoidal pattern;
- a left side and a right side truncating the first intermittent sinusoidal pattern and the second sinusoidal pattern for each of the plurality of grating elements;
- wherein the plurality of grating elements in the plurality of columns are connected by a web extending from the top side of one grating element to the bottom side of an adjacent grating element; and
- wherein the plurality of grating elements form a plurality of rows of grating elements extending for several grating periods of the first intermittent sinusoidal pattern perpendicular to the plurality of light emitters forming a gap between the left side of one grating element and the right side of an adjacent grating element in the row.

17. The intensity modulating element of claim 16, wherein the length of the grating period is at least two times greater than the width of the plurality of light emitters.

18. The intensity modulating element of claim 16, wherein the amplitude of the first intermittent sinusoidal pattern is at least five times less than the length of the plurality of light emitters.

19. The intensity modulating element of claim 16, wherein the substrate of the intensity modulating element is made of sapphire.

20. The intensity modulating element of claim 16, wherein the plurality of grating elements are formed using a coating that is highly absorptive of the wavelengths emitted by the light emitters.

* * * * *

UNITED STATES PATENT AND TRADEMARK OFFICE
CERTIFICATE OF CORRECTION

PATENT NO.         : 8,422,030 B2                          Page 1 of 1
APPLICATION NO.    : 13/100826
DATED              : April 16, 2013
INVENTOR(S)        : Clark Alexander Bendall et al.

It is certified that error appears in the above-identified patent and that said Letters Patent is hereby corrected as shown below:

In the Claims

Col. 17, claim 5, line 63, please change to the following:

and is the mirror image of the first intermittent triangle pattern;

Signed and Sealed this
Thirtieth Day of December, 2014

Michelle K. Lee
*Deputy Director of the United States Patent and Trademark Office*